(12) United States Patent
Cai (10) Patent No.: US 11,903,558 B2
(45) Date of Patent: Feb. 20, 2024

(54) INTRACARDIAC IMAGING CATHETER

(71) Applicant: John Jun Cai, Williamsville, NY (US)

(72) Inventor: John Jun Cai, Williamsville, NY (US)

(*) Notice: Subject to any disclaimer, the term of this patent is extended or adjusted under 35 U.S.C. 154(b) by 528 days.

(21) Appl. No.: 16/843,670

(22) Filed: Apr. 8, 2020

(65) Prior Publication Data
US 2020/0315431 A1 Oct. 8, 2020

Related U.S. Application Data

(60) Provisional application No. 62/830,737, filed on Apr. 8, 2019.

(51) Int. Cl.
| | | |
|---|---|---|
| *A61B 1/00* | (2006.01) | |
| *A61B 1/07* | (2006.01) | |
| *A61M 25/10* | (2013.01) | |

(52) U.S. Cl.
CPC ...... *A61B 1/00117* (2013.01); *A61B 1/00082* (2013.01); *A61B 1/00119* (2013.01); *A61B 1/00135* (2013.01); *A61B 1/07* (2013.01); *A61M 25/1002* (2013.01)

(58) Field of Classification Search
None
See application file for complete search history.

(56) References Cited

U.S. PATENT DOCUMENTS

| | | | |
|---|---|---|---|
| 5,330,490 A * | 7/1994 | Wilk | A61B 17/068 623/1.1 |
| 5,588,952 A | 12/1996 | Dandolu | |
| 7,534,204 B2 | 5/2009 | Starksen | |
| 2004/0097788 A1* | 5/2004 | Mourlas | A61B 1/005 600/116 |
| 2005/0228452 A1* | 10/2005 | Mourlas | A61M 25/1002 606/41 |
| 2014/0180007 A1* | 6/2014 | Edidin | A61B 1/00082 600/122 |
| 2016/0143522 A1* | 5/2016 | Ransbury | A61B 5/0071 600/116 |

* cited by examiner

*Primary Examiner* — Timothy J Neal
(74) *Attorney, Agent, or Firm* — Vincent G. LoTempio; David T. Stephenson (57) ABSTRACT

A direct intracardiac imaging catheter capable of entering chambers of the heart and providing an image through a vein or an artery percutaneously, or through direct access during open surgery. The intracardiac imaging catheter apparatus is a small optical fiber imaging system. The catheter is deflectable and capable of navigating within all heart chambers to acquire detailed images, and adjacent large vessels during percutaneous cardiac procedures. The catheter can access the arterial system to acquire blood vessel images. It can pass through the intra-atrial septum (foramen ovale) for cardiac procedures in the left chambers and large vessels adjacent the left heart, including pulmonary veins and the aorta. During open heart surgery, images can be provided from hard to access regions including the back of the heart during off pump cardiac surgery. The apparatus includes balloon tip that can be inflated and deflected based the movement of catheter.

15 Claims, 6 Drawing Sheets

INTRACARDIAC IMAGING CATHETER

CROSS-REFERENCE TO RELATED APPLICATIONS

This application claims priority under 35 U.S.C. § 119(e) to U.S. Provisional Application No. 62/830,737, filed Apr. 8, 2019, the entire disclosure of which is herein incorporated by reference.

TECHNICAL FIELD

The present disclosure relates to a direct intracardiac imaging (DICI) catheters, particularly but not exclusively catheters capable of entering chambers of the heart and providing an image for diagnostic and treatment purposes.

BACKGROUND

Within the heart, bodily fluids such as blood generally make in vivo real time imaging of cardiac structures very difficult. Intracardiac catheters are known to utilize ultrasound imaging as an image modality to visualize the heart because the direct intracardiac imaging technique is largely limited by blood filled heart chambers and narrow passages. A number of different methods, other than direct visual imaging, have been used to visualize interior regions of a patient's body by depicting a visual construct, either by ultrasound or a computer-generated mapping system. In computer generated mapping devices having position sensors outside of body as a reference point while confirm with a real time fluoroscopic imagine then creates. For example, two- or three-dimensional image of a patient's internal organs and cardiac structures are known in the art.

Current standard visualization of minimally invasive percutaneous cardiac procedures is typically accomplished by echocardiogram or 3D computer-generated mapping devices. Although these techniques work relatively well for some cardiac procedures, it does not provide as clear a picture of the surgical site as would direct visualization. All type of echocardiograms, transthoracic echocardiogram (TTE), transesophageal echocardiogram (TEE), intracardiac echocardiogram (ICE) and intravascular cardiogram (IVUS) are based on contrast differences between liquid and solid phase and subject to operator interpretation as well as software manipulation. Small inaccuracies can be greatly magnified, thereby resulting in errors and legal liability.

Computer generated 3D mapping has been widely used for invasive percutaneous cardiac procedures. However, this method heavily depends on fluoroscopic confirmation with large radiation exposure, and computer reconstruction providing an external reference does not include patient position and operator position. These methods require extensive software modification and extensive training in order to understand the images. Thus, few cardiologists are truly proficient in interpreting such images. Additionally, visual information provided by such devices may be limited because a mapping device may not be able to provide visual information regarding the tissue surface condition within a heart chamber.

Endoscopic imaging devices are known to use an inflatable imaging balloon for obtaining in vivo imaging of a patient's tissue regions. The imaging balloon can be introduced into the patient's body in a deflated state. Once introduced, the imaging balloon can be inflated and pressed against a targeted tissue region for imaging. Balloon-covered endoscope devices may be introduced into the surgical site through a sheath or introducer device separately from any of the instruments used to perform the cardiac procedure. In balloon endoscope devices, the endoscope must be advanced to the surgical site to visualize the site. The endoscope may generally include a sheath with an expandable balloon at the distal end and an inflation lumen for expanding the balloon.

Visualization of the inner components of the heart is critical for diagnosis and treatment of many cardiac problems. Current standard methods of visualization of the heart generate composite, unclear digital images. While the images provided by current methods are useful, they do not provide the full scope of data necessary for proper diagnosis and treatment.

Optical fibers are known to be used in endoscopy. However, generating a viable image from the heart has proved to be challenging. For example, the heart has chambers that have been difficult to access, due to small access points, and difficult to image with conventional technology. In a fiber optic cable, many individual optical fibers are bound together around a central steel cable or high-strength plastic carrier for support. This core is then covered with protective layers of materials such as aluminum, Kevlar, and polyethylene (the cladding). Because the core and the cladding are constructed of slightly differing materials, light travels through them at different speeds.

There are two types of optical fibers. In a single-mode fiber, the core is smaller, typically 10 micrometers (a micrometer is one-millionth of a meter) in diameter, and the cladding is 100 micrometers in diameter. A single-mode fiber is used to carry just one light wave over very long distances. Multimode optical fibers, which have a core diameter of 50 micrometers and a cladding diameter of 125 micrometers, can carry hundreds of separate light wave signals over shorter distances. This type of fiber is used in urban systems where many signals must be carried to central switching stations for distribution. Yeh, Chai. Handbook of Fiber Optics. Academic Press, 1990. Optical fibers present the opportunity for a small diameter catheter that can access all regions of the heart for imaging through endoscopy.

Recent data published by University of Wisconsin in Nature Communications, 2014 show that by use of a fiber consisting of two randomly distributed polymers, which scatter light. The disordered interior of the fiber causes a beam of light passing through it to freeze, accommodating multiple beams. The optical fiber provides a direct one-to-one image transfer with less pixilation and higher contrast (Nature Communication (2014); doi:10.1038). This imaging technique is contemplated within the scope of the present disclosure and is herein incorporated by reference.

Recent advancements in minimal invasive percutaneous cardiac procedures from electrophysiology ablation procedures to percutaneous valve replacement create a significant challenge in obtaining adequate images with clear detail. Direct intra-cardiac images are difficult to obtain due to complex structures in heart chambers filled with blood. Thus, there is a need for medical devices that can provide improved visualization for viewing the heart.

SUMMARY

The present disclosure solves problems associated with conventional cardiac imaging. The present disclosure device may be used for imaging, and may be adapted to for use with adopt surgical treatment devices. However, the lack of surgical tools included with the fiber optic line allows the catheter to be narrower and have greater access to regions of the heart otherwise inaccessible to conventional cardiac catheters. The device can pass through the intra-atrial septum through foramen ovale for left heart structural images, or cannulate coronary sinus. Intravascularly, it should be able to cannulate the large aorta and large size coronary arteries or ostium of a blood vessel. The device of the present disclosure includes a self-contained air balloon tip that may be inflated upon reaching a region of interest to create temporary air chamber for fiberoptic imaging without affecting blood flow within heart chambers.

Medical devices may, in some cases, use an inflatable balloon to move inside heart chambers and large vessels to record hemodynamic data. However, combining use balloon and imagine technology has not be well defined. The imaging balloon as we introduced here is unique system that our catheter not only be able to move freely within the heart but also the air or sailing solution filled balloon tip can temporarily provide a lighted environment with high intensity light source comes in with the catheter. The present catheter, in some embodiments, may be designed having at least three components: 1) a movable metal spring wire, 2) an illuminating light optical fiber cable connected to the battery power within the control handle, and 3) a catheter that connects to a digital and optical lens within the control handle, then connects to a semiconducting motherboard that provides a digital filter and necessary digitization. The optical fiber catheter of the present disclosure may include an inflation lumen within the central support cable which may be found in conventional optical fiber cables.

BRIEF DESCRIPTION OF THE DRAWINGS

The present disclosure will now be further and more particularly described, by way of example only, and with reference to the accompanying drawings in which.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. Furthermore, there is no intention to be bound by any expressed or implied theory presented in the preceding technical field, background, brief summary or the following detailed description. It is also to be understood that the specific systems and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The imaging catheter 100 of the present disclosure solves problems associated with conventional cardiac imaging catheters. As shown in FIGS. 1-6, in one embodiment of the present disclosure, imaging catheter 100 may be used for imaging, thereby allowing a fiber optic catheter 20 to be narrower in diameter and provide greater access to and images of regions of the heart 28 (shown in FIG. 2) otherwise inaccessible for conventional intracardiac imaging catheters. In the present disclosure, an expandable balloon coupled with a distal end of the elongate sheath is inflated and the location in the heart is visualized through the expandable balloon, using at least one visualization device disposed in the elongate sheath.

Figure 1:
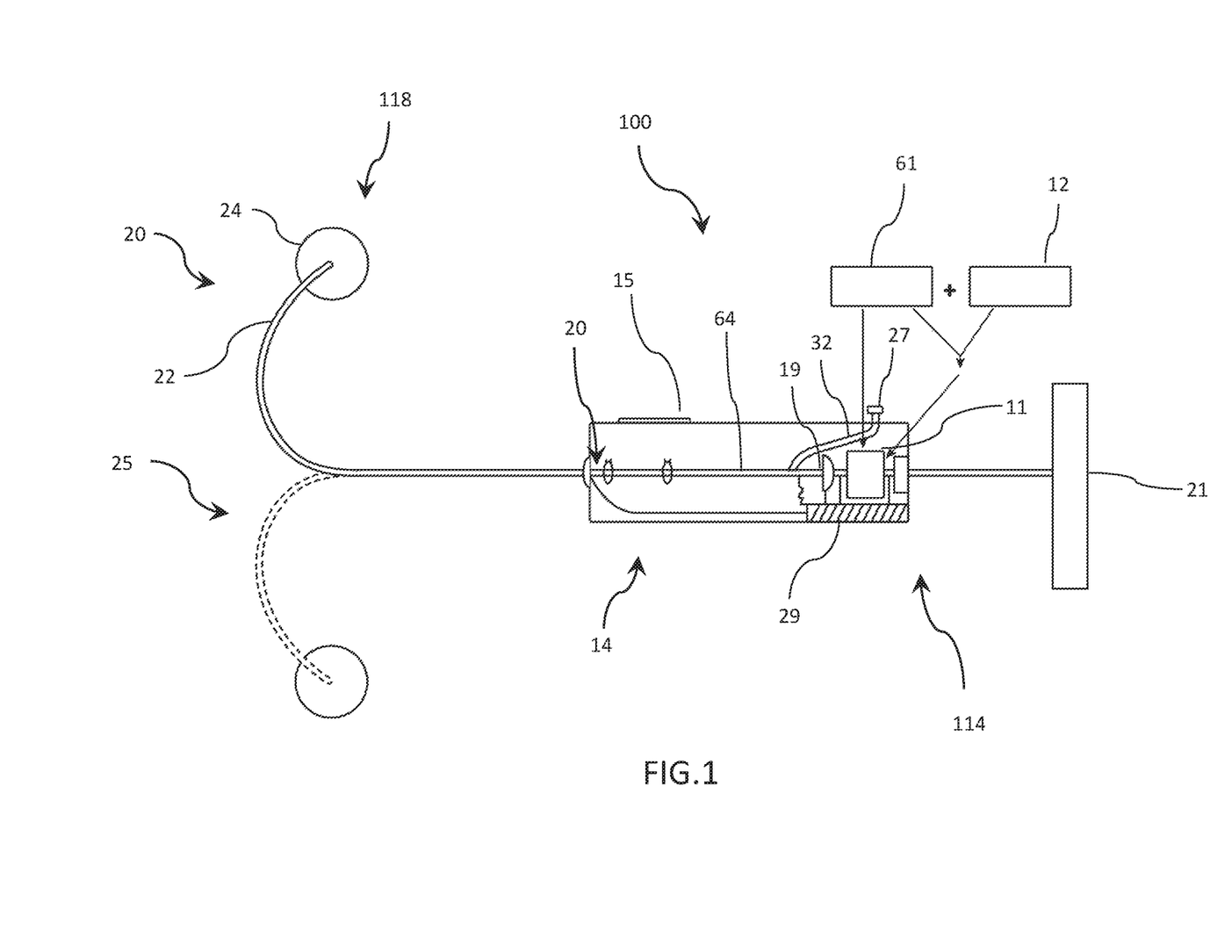
FIG. 1 shows a side cross sectional view of the imaging catheter apparatus of the present disclosure.

Referring now to FIG. 1, an exemplary imaging catheter apparatus 100 can be used to visualize tissue structures within a human anatomy. Imaging catheter apparatus 100 includes a catheter 20 (which may also be described as an elongate shaft) having a proximal end portion 114 and a distal end portion 118. In some embodiments, proximal end portion 114 can couple to a catheter hub or a manifold. In the depicted embodiment, the distal end portion 118 includes at least one balloon 24. In some embodiments, catheter 20 may be 80 cm in length.

In some embodiments, optical fiber imaging cable 24 has distal end portion 118 extending into balloon 24. In other embodiments, distal end portion 118 may be flush with, or recessed into, the distal end portion 118 of catheter 20. Thus, there is no requirement that any visualization member extend into balloon 24. Lens 19 may, in one embodiment, be positioned at distal end portion 118 of the optical fiber imaging cable 20, between interface 11 and optical fiber imaging cable 20.

Optical fiber catheter 20 transmits information directly to a user. In one embodiment, information may be transmitted to a monitor 21. Interface 11 may be custom designed. Interface 11 may feed an electrical signal into a computer to obtain an image. Software 12 may interact with the interface 11. In some embodiments, a central processing unit (CPU) may be used to process images of the surgical site. Shown in FIG. 1 is filter and digitizer 61. Such processed images may then be transmitted for viewing by the physician.

With further regard to FIG. 1, a battery 29 may be connected to a light source in handle 14. The handle 14 may also contain a syringe port, which may be a fluid injector port 27. Handle 14 also may include port connector tube 32 to transfer inflation fluid or other inflation material. Catheter 20 may transmit information directly to a user through a fiber optic imaging cable 64. In one embodiment, information may be transmitted through a monitor 21.

A battery 29 may be connected to a light source in handle 14. Imaging catheter apparatus 100 may preferably include a bi-directional means of guiding catheter 20 to a desired location within heart 28, represented as second position 25 in FIG. 1. In one embodiment, catheter 20 is deflectable. U.S. Pat. Nos. 9,233,225, 4,739,786, 6,726,700 and 7,591,813 disclose deflectable catheters that may be used in conjunction with the present disclosure, and these patents are herein incorporated by reference. Catheter 20 may be unidirectional or bidirectional.

In these and other embodiments, a central processing unit may be used to process captured images of the visualization site. Such processed images may then be transmitted for viewing by the physician. For example, in one embodiment visualization may be achieved using a light source at handle 14 and optical fiber imaging cable 64.

Balloon 24 may be inflated within a heart 28. The balloon 24 is attached at the distal end of catheter 20, such that when balloon 24 is inflated it removes obstructing fluids from interfering with observation by the imaging cable at a terminus of the fiber optic catheter 20. The balloon 24 of the present disclosure may preferably have a dome shape and is preferably transparent. The shape of balloon 24, once inflated, allows for a circumspect view of the cardiac region of interest, without interference from fluids.

Balloon 24 is intended to be small enough for the purposes of the present disclosure, which include accessing and visualizing all chambers of the heart 28. Imaging catheter device, systems, and methods provided herein can allow for visualization of a target location, which can provide anatomy and pathology identification as well as device placement visual feedback to the physician user during a minimally invasive method. Balloon catheter visualization devices, systems, and methods provided herein may include a round, dome-shaped, or elongate compliant balloon of various shapes having a transparent wall.

A distal end distal end portion 118 can be either directly or indirectly coupled to a balloon 24. For example, catheter 20 can be coupled to balloon 24 indirectly by using an intermediate catheter shaft. The intermediate catheter shaft can couple to a proximal end of balloon 24. Alternatively, balloon 24 can be directly coupled to catheter 20 using an adhesive, as would be known to one of ordinary skill in the art.

In some embodiments, balloon 24 is disposed at or near to distal end portion 28 of catheter 20. Balloon 124 can include the proximal end, a distal end and a wall that extends from an interior surface to an exterior surface. In the depicted embodiment, balloon 24 forms a distal tip of imaging catheter apparatus 100. As described further herein, balloon 24 can be filled with an inflation media in an interior cavity defined between proximal and distal ends.

Figure 3:
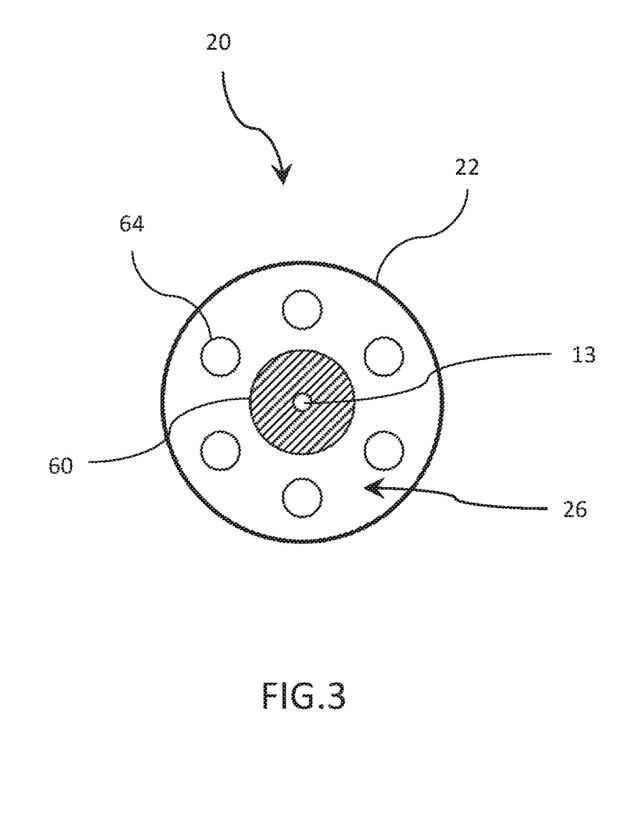
FIG. 3 shows a front cross-sectional view of the catheter according to the present disclosure.

Inflating the balloon typically involves injecting a fluid or air into the balloon via an inflation lumen, which may be incorporated into support cable 60 (as shown in FIG. 3), though any other inflation method may be used. There may be, in some embodiments, a port for air and a port for fluid, for inflation of the present device. The balloon 24 may preferably have a dome shape, however, in some embodiments of the invention it may have any shape, such as a toroidal balloon encircling the at least one lumen or a spherical or ovoid balloon adjacent at least one lumen.

In some embodiments, balloon 24 may have any suitable size, shape and configuration and may be made from any suitable expandable material. Although a dome shaped balloon may be preferred, alternative embodiments may include a spherical, ovoid or otherwise shaped balloon disposed adjacent a lumen. Similarly, any suitable inflation lumen 13 may be included in sheath 22 for expanding balloon 24. Inflation lumen 13 may comprise a circumferential lumen. Inflation lumen 13 may be a channel extending from a proximal end of the catheter 20 to a distal end of the catheter 20. Any means for inflating balloon 24 is contemplated within the scope of the invention. Typically, balloon 24 is inflated by introducing a fluid, such as saline, or by introducing air, into balloon 24 via inflation lumen 13, although any other inflation technique or substance may be used.

Optionally, methods may further include passing at least one fluid through a lumen to flush the location for performing the procedure and/or to cleanse one or more instruments. Also, optionally, a method may include retracting an outer tubular member to expose expandable balloon material from the distal end of the sheath and inflating the expandable balloon 24.

In some embodiments, the balloon wall is translucent, expandable, and is comprised of silicone, which may be about 30 A durometer. It should be understood that other combinations of materials are also envisioned. In another non-limiting example, the balloon wall is made of silicone at a first durometer (e.g., about 30 A durometer) and the reinforcement material is made of silicone at a second durometer (e.g., about 50 A durometer). Various materials can be used for the balloon wall. In one non-limiting example, the balloon wall is silicone. In some embodiments, the balloon wall can be formed by dip-molding. In an inflated state, in one embodiment the balloon may have a general width or diameter of 1.5-2 cm in at least one direction. In one embodiment, balloon 24 may be inflated to 2-3 cc. In a deflated state, balloon 24 may be wrapped around catheter 20. Balloon 24 may be attached to catheter 20 with an adhesive.

Balloon 24 may be coupled with an outer tubular member at an attachment point such that sliding outer tubular member proximally and introducing additional fluid or other inflating substance into balloon 24 will cause balloon 24 to further expand. Any suitable configuration of balloon material and an attachment point may be used. In one embodiment, for example, balloon material may be housed in a small slit or housing coupled with outer tubular member. Balloon expansion, for example, may help exclude additional blood and/or push aside surrounding tissue from the surgical site.

Figure 2:
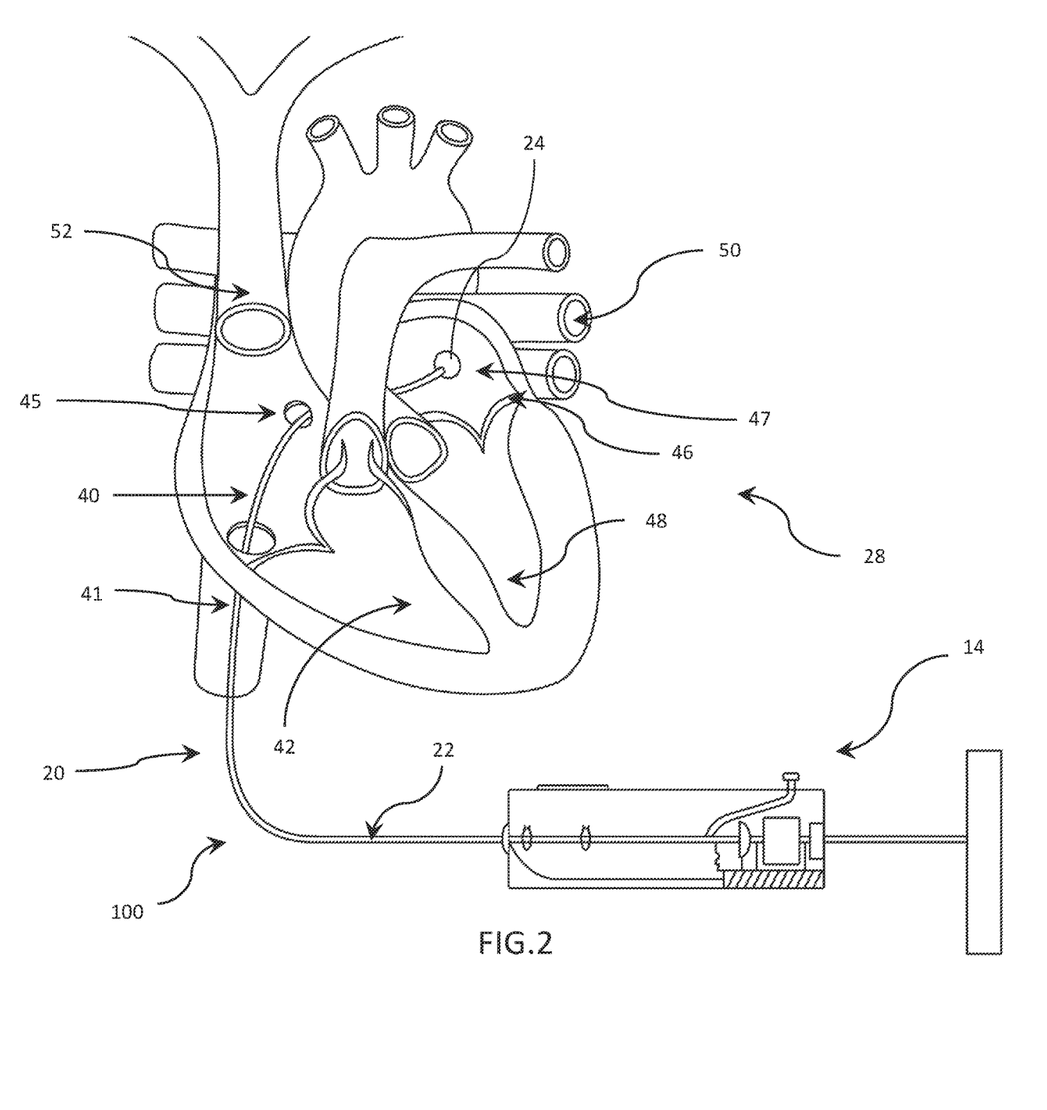
FIG. 2 shows a side cross sectional view of the imaging catheter apparatus of the present disclosure inserted within a heart.

Referring now to FIG. 2, in some cases, imaging catheter apparatus 100 can be inserted into a right atrium of a heart 28 through a brachial vein or a jugular vein. In some embodiments, the elongate sheath 22 of catheter 20 may be flexible and deflectable to a second position 25 (as shown in FIG. 1) so that it may be advanced through the vasculature of a patient to position at least a distal portion of the sheath in the heart 28. In some embodiments, the apparatus of the present disclosure may pass through the intra-atrial septum through the foramen ovale 45 for left heart structural images. For intravascular uses, the device of the present disclosure can visualize large vessel plaques, narrowing, and dissection points within vessels.

For example, the sheath 22 may be advanced through the internal jugular vein, superior vena cava 52, right atrium 40 and interatrial septum of the patient to position the distal portion of the sheath in the left atrium 47. Alternatively, the sheath 22 may be advanced through the internal jugular vein, superior vena cava 52, right atrium 40, coronary sinus and left atrial wall of the patient to position the distal portion of the sheath in the left atrium 47. In still another embodiment, sheath 22 and catheter 20 may be advanced through the femoral vein, inferior vena cava 41, right atrium 47 and interatrial septum. In other embodiments, the sheath may be rigid and may be introduced thoracoscopically, or otherwise through the heart wall. Other structures of the heart that are relevant to use of the method and apparatus of the present disclosure include right ventricle 42, left inferior pulmonary vein 44, left atrial appendage 46, left ventricle 48 and left superior pulmonary vein 50.

Generally, sheath 22, and thereby catheter 20, may be flexible, rigid, or part-flexible part-rigid, and may be introduced to a surgical site via any suitable method or route. For example, sheath 22 may be advanced to the mitral valve of heart 28 through the superior vena cava, right atrium, foramen ovale, and left atrium. Access to the superior vena cava 52 may be gained, for example, via the internal jugular vein. In other embodiments, access to the right atrium may be gained through the femoral vein and the inferior vena cava 41. Thus, access to the heart may be achieved via a transvascular route. Alternatively, sheath 22 may be introduced through an incision and/or access port in the wall of the left atrium 47. Any other suitable minimally invasive means for gaining access may alternatively be used to position sheath 22, and catheter 20, in a desired location for visualization.

Figure 4:
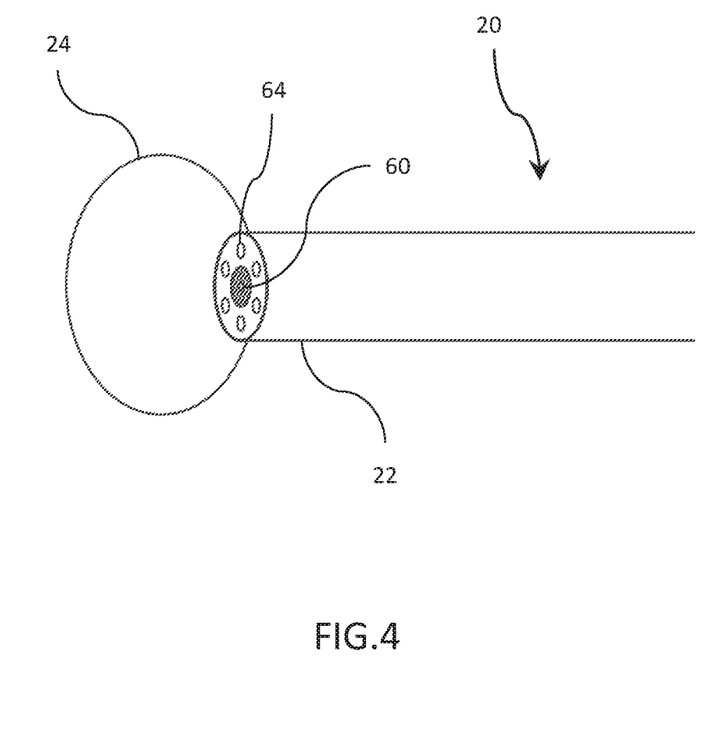
FIG. 4 shows a front perspective view of the distal end portion of the catheter according to the present disclosure.

Referring now to FIGS. 3 and 4, imaging catheter apparatus 100 can include an elongate catheter 20 with a distal end portion 118. Catheter 20 may, in some embodiments, preferably be 2.1 mm in diameter. Sheath 22 of catheter 20 may comprise any suitable material or combination of materials and may have any suitable shape, size, diameters, thicknesses and the like. In various embodiments, components of catheter 20, including sheath 22, may be flexible along their entire lengths, rigid along their entire lengths or part-flexible, part-rigid. The components may be composed of one or more metals, such as Nitinol, stainless steel or titanium; flexible or rigid polymers, such as polyurethane, polytetrafluoroethylene (PTFE), other fluoropolymers, PEBAX®, and/or the like; or any other suitable material or combination of materials. In some embodiments, tubular members may be rigidly fixed to one another, while in other embodiments one of the members may be movable relative to the other. For example, in one embodiment an outer tubular member is slidably disposed over an inner tubular member so that it can retract proximally over inner tubular member and then extend back distally to its original position.

Cable lumen 26, enclosed by sheath 22 and containing cables, may have any suitable size, diameter and the like and may be disposed in any location through sheath 22 (which may preferably have a diameter of 2.1 mm), an may include at least one fiber optic imaging cable 64 and a support cable 60. In embodiment cable lumen 26 comprises six optical fiber imaging cables 64 encircling support cable 60 in a symmetric, evenly-space circular configuration. Optical fiber imaging cables may be either single mode or multi-mode, as contemplated by the present disclosure. Thus, cable lumen 26 may open into balloon 24, or may alternatively open adjacent (but not through) balloon 24. In some embodiments, cable lumen 26 may allow passage of any suitable device or devices. Any and all suitable devices are contemplated.

Cable lumen 26 may include support cable 60, which may be comprised of a rigid or semi-rigid material. Materials for support cable 60 may, without limitation, include aluminum, steel, or plastics, as would be suited for the purposes of the present disclosure. Support cable 60 may include an inflation lumen 13 that is in fluid communication with fluid injection port 27 and port connector tube 32. Support cables are utilized in conventional optical fiber cables to support the optical fibers surrounding the support cable. In the present disclosure, a channel is introduced within support cable 60 to provide inflation material, such as saline solution, to the balloon 24. In order to maximize efficiency of space in the small catheter 20 so that it can access difficult to reach regions of the heart, inflation lumen 13 was combined with support cable 60, to create a dual function cable. Support cable 60 therefore provides both support to the optical fiber imaging cables 64 surrounding support cable 60, and also provides inflation material to balloon 24 at the distal end portion 118 of catheter 20. Support cable 60 is generally comprised of a strong, relatively thick in diameter portion of catheter 20, and therefore provides a safe and reliable structure to serve as a conduit for inflation material such as air or saline solution.

Imaging catheter apparatus 100 includes at least one fiber optic imaging cable 64. Light may be transferred through fiber optic imaging cable 64 to illuminate a target region or any other material capable of transmitting light through catheter 20 in a cable. A light source transmits light to optical fiber imaging cable 64, as would be known to one of ordinary skill in the art. The light source may be an incandescent or LED lamp, laser, or any other light source known in the art for transmitting light through an optical fiber cable, as would be known to one of ordinary skill in the art. In some embodiments, a light source would be surrounding the optical fiber imaging cable 64. The visualizing step according to the present disclosure may be performed using optical fiber visualization. Visualization data may be returned through optical fiber imaging cable 64 for viewing by a physician.

In some embodiments, imaging catheter apparatus 100 includes at least one catheter 20 defining at least one lumen. Each catheter 20 may optionally include multiple lumens, for example, coaxial or non-coaxial lumens. Lumens may exist for optical fiber imaging cable 64, deflection cables or other devices that could be used in accordance with the present disclosure. Imaging catheter apparatus 100 may have one or more lumens that extend partially or fully thorough catheter 20. One or more lumens can be used as a conduit adapted to receive components, e.g., inflation media, e.g., saline. In some cases, one or more lumens, such as inflation lumen 13 (shown in FIG. 3) can be adapted to jet inflation media, e.g., saline, into distal end portion 118 of imaging catheter apparatus 100.

In some embodiments catheter 20 may include a plurality of lumens where each lumen can be formed from one of various cross-sectional shapes, e.g., circle, oval, slot, square, rectangular, triangular, trapezoid, rhomboid, or irregular shape. The shape of the lumen may facilitate receiving other components of imaging catheter apparatus 100. For example, one or more lumens can be used to receive fiber optic light cables, inflation media, additional components and combinations thereof.

In some embodiments, catheter 20 includes a central lumen for receiving two or more lumens for receiving optical fiber light cables 64, and one or more lumens for delivering inflation media, and at least one optical fiber imaging cable. Catheter 20 of intracardiac imaging catheter apparatus 100 is, in some embodiments, able to pass through a septum due to its narrow diameter. With further regard to the diameter of imaging catheter apparatus 100, at the distal end portion 118, in one embodiment of the intracardiac imaging catheter apparatus 100, catheter 20 has an 8.5 French deflector lumen formed from sheath 22 for receiving at least one optical fiber imaging cable 64.

Figure 5:
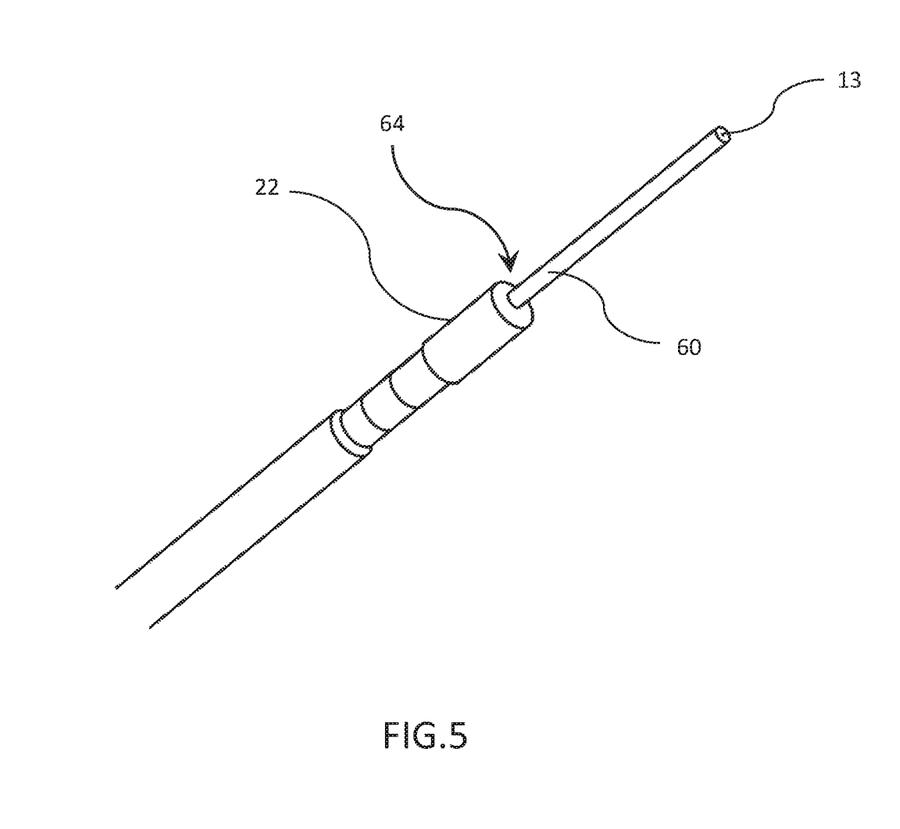
FIG. 5 shows a front perspective view of one embodiment of the distal end portion of the imaging catheter apparatus according to the present disclosure.

Referring now to FIG. 5, in one embodiment of the present invention, support cable 60, which may be comprised of a metal such as aluminum or steel, or other semi-rigid or rigid material, extends beyond the termination of optical fiber imaging cables 64 at distal end portion 118 of imaging catheter apparatus 100. In this embodiment, optical fiber imaging cables are severed, symmetrically, prior to the termination point of distal end 118 of imaging catheter apparatus 100. The extended portion of support cable 60, which includes inflation lumen 13, may provide support for a balloon 24 in a deflated or inflated state.

Figure 6:
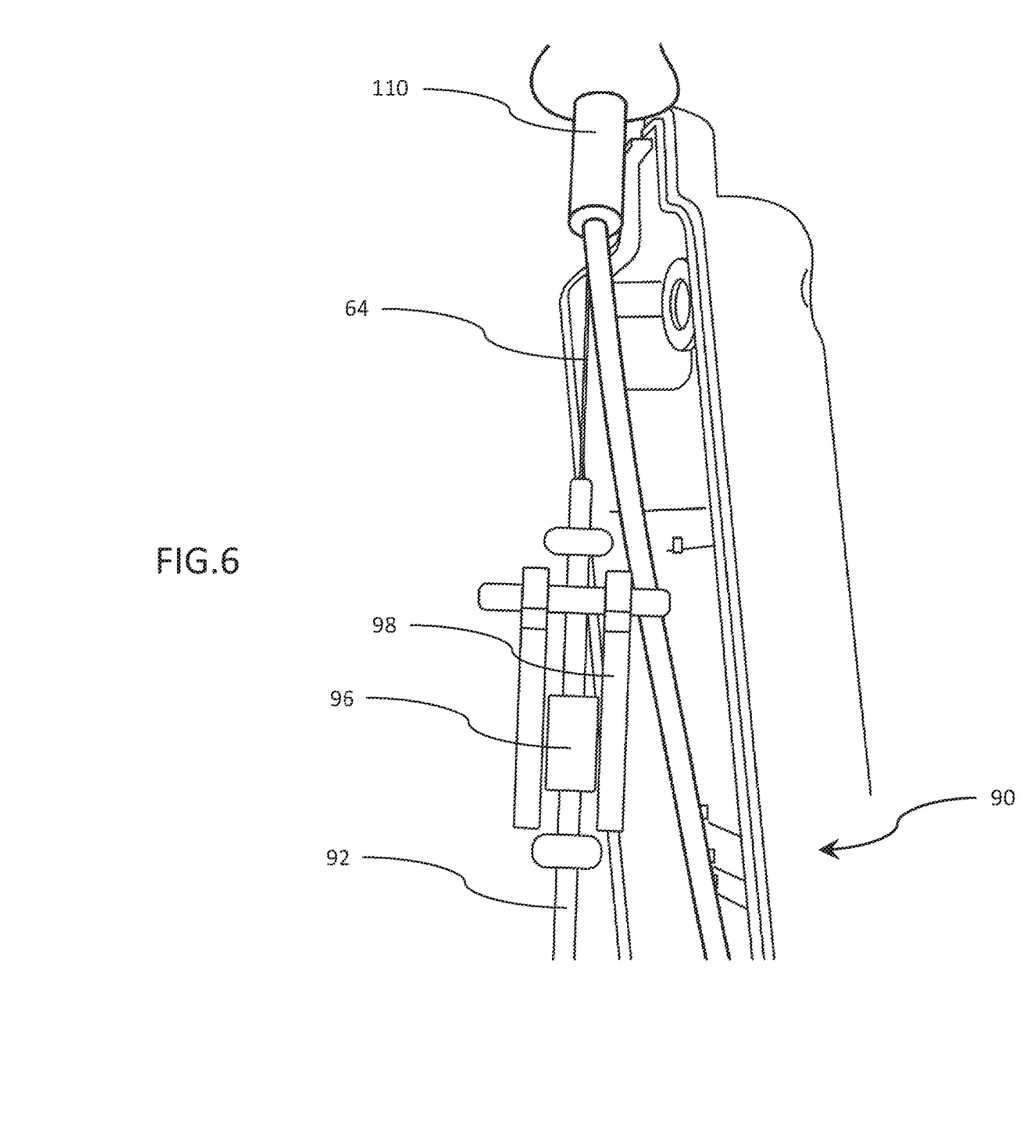
FIG. 6 shows an internal exploded perspective view of the handle of the imaging catheter apparatus according to the present disclosure.

Referring now to FIG. 6, a perspective exploded view of handle 14 shows various components inside control cover 90. These components include a catheter stabilizer within control handle chamber 110, an optical fiber imaging cable 64, an optical fiber cable control apparatus 98, a rubber ring 96 to stabilize optical fiber imaging cable 64, and an insulating cable shield 92.

Methods of the present invention generally involve first advancing catheter 20, and sheath 22, to a location in the heart 28. Next, expandable balloon 24 is inflated and a visualization device is used to visualize an area within the heart 28 and locate an area of interest. During the procedure, real-time visualization may be acquired via, in one embodiment, optical fiber imaging cable 64. Imaging cable 64 may be used to assess the site, locate a particular structure, and reposition sheath 22 for better visualization and/or access to the site.

Imaging catheter apparatus 100 may be placed in the right side of heart through the femoral vein, or internal jugular vein or subclavian vein. Imaging catheter apparatus 100 may be useful in accessing or cannulating the coronary sinus; a continual challenge for cardiac electrophysiologists. The device of the present disclosure can be retrograded to enter left heart through aorta via femoral artery access. The device of the present disclosure may also pass through the intra-atrial septum through the foramen ovale 45 for left heart structural images. For intravascular uses, the device of the present disclosure can visualize large vessel plaques, narrowing, and dissection points within vessels.

In many embodiments, optical fiber imaging cable 64 may be moved within sheath 22 and/or multiple visualization devices may be used to acquire images from different perspectives and angles. Adjustments to the size of balloon 24 may be made. The device may be adapted to for use with procedural or surgical treatment devices including but not limited to ablation or surgical clips. Any other suitable method steps may be added, in accordance with the present disclosure, and steps may be skipped or combined, and or alternative steps may be substituted without departing from the scope of the invention. In some embodiments, the physician may also flush one or more portions of sheath with a fluid passed through one of the sheath's lumens.

Although various embodiments of the present invention have been described fully above, this description is for exemplary purposes only and should not be interpreted to limit the scope of the invention. For example, various alterations, additions, substitutions or the like may be made to embodiments described above without departing from the scope of the invention. Therefore, none of the foregoing description should be read to limit the scope of the invention as it is defined in the following claims.

Any and all patents, applications and printed publications mentioned above are hereby incorporated by reference.

What is claimed is:

1. An imaging catheter apparatus, comprising:
a catheter having a proximal end portion and a distal end portion, wherein the catheter is comprised of a sheath, a plurality of optical fiber imaging cables and a support cable;
wherein the sheath encloses the plurality of optical fiber cables and the support cable;
wherein the plurality of optical fiber cables encircle the support cable;
wherein the support cable comprises an inflation lumen;
wherein the plurality of optical fiber cables terminate at the distal end portion of the catheter;
wherein the sheath terminates at approximately a same radial plane at the distal end portion of the catheter as the plurality of optical fiber cables;
wherein the sheath at the distal end portion of the catheter is adhered to an opening portion of a balloon with an adhesive;
wherein the inflation lumen is in fluid communication with an internal portion of the balloon.

2. The imaging catheter apparatus of claim 1, wherein the support cable is comprised of a metal and is encircled by the plurality of optical fiber imaging cables, wherein the optical fiber imaging cables comprise at least six optical fiber imaging cables; and
wherein the support cable includes a lumen extending from a proximal end of the catheter to a distal end of the catheter.

3. The imaging catheter apparatus of claim 1, wherein the support cable extends beyond the optical fiber imaging cables in a distal direction at the distal end portion of the catheter.

4. The imaging catheter apparatus of claim 1, wherein the support cable is encircled by the plurality of optical fiber imaging cables, wherein the optical fiber imaging cables comprise at least six optical fiber imaging cables.

5. The imaging catheter apparatus of claim 1, wherein a diameter of the catheter is 2.1 mm or less.

6. The imaging catheter apparatus of claim 1, wherein the balloon is comprised of silicone having a durometer of 30 A.

7. The imaging catheter apparatus of claim 1, wherein an inflation media is a saline solution.

8. The imaging catheter apparatus of claim 1, wherein the balloon is dome-shaped.

9. The imaging catheter apparatus of claim 1, wherein the support cable is in fluid communication with a fluid injector port.

10. The imaging catheter apparatus of claim 1, wherein the support cable is hollow.

11. The imaging catheter apparatus of claim 1, wherein the support cable is comprised of aluminum.

12. An imaging catheter apparatus, comprising:
a catheter having a proximal end portion and a distal end portion, wherein the catheter is comprised of a sheath, a plurality of optical fiber imaging cables and a support cable;
wherein the sheath encloses the plurality of optical fiber cables and the support cable;
wherein the plurality of optical fiber cables encircle the support cable;
wherein the support cable comprises an inflation lumen;
wherein the plurality of optical fiber cables terminate at the distal end portion of the catheter;
wherein the sheath terminates at approximately a same radial plane at the distal end portion of the catheter as the plurality of optical fiber cables;
wherein the sheath at the distal end portion of the catheter is adhered to an opening portion of a balloon with an adhesive;
wherein the inflation lumen is in fluid communication with an internal portion of the balloon;

wherein the support cable extends beyond the optical fiber cables in a distal direction at the distal end portion of the catheter;

wherein the support cable comprises an inflation lumen; wherein the support cable is hollow;

and, wherein an inflation media is a saline solution.

13. The imaging catheter apparatus of claim 12, wherein a diameter of the catheter is 2.1 mm or less.

14. The imaging catheter apparatus of claim 12, wherein the support cable is symmetrically encircled by the plurality of optical fiber imaging cables, wherein the optical fiber imaging cables comprise at least six optical fiber imaging cables.

15. The imaging catheter apparatus of claim 12, wherein a portion of the support cable that extends beyond the plurality of optical fiber imaging cables in a distal direction is in contact with an inner portion of the balloon when the balloon is in a deflated state.

* * * * *